United States Patent
Højlund Nielsen et al.

(10) Patent No.: US 10,987,646 B2
(45) Date of Patent: Apr. 27, 2021

(54) DEHYDROGENATION OF ALKANES

(71) Applicant: HALDOR TOPSØE A/S, Kgs. Lyngby (DK)

(72) Inventors: Poul Erik Højlund Nielsen, Fredensborg (DK); Rasmus Munksgård Nielsen, Måløv (DK); John Bøgild Hansen, Humlebæk (DK); Burcin Temel McKenna, Hellerup (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 15/769,450

(22) PCT Filed: Oct. 24, 2016

(86) PCT No.: PCT/EP2016/075489
§ 371 (c)(1),
(2) Date: Apr. 19, 2018

(87) PCT Pub. No.: WO2017/072057
PCT Pub. Date: May 4, 2017

(65) Prior Publication Data
US 2018/0311630 A1    Nov. 1, 2018

(30) Foreign Application Priority Data
Oct. 28, 2015 (DK) .......................... PA 2015 00662

(51) Int. Cl.
*B01J 8/00* (2006.01)
*B01J 8/02* (2006.01)
(Continued)

(52) U.S. Cl.
CPC .......... *B01J 8/0285* (2013.01); *B01J 19/087* (2013.01); *B01J 23/08* (2013.01); *B01J 23/745* (2013.01);
(Continued)

(58) Field of Classification Search
CPC ..... B01J 8/00; B01J 8/02; B01J 8/0285; B01J 19/00; B01J 19/08; B01J 19/087;
(Continued)

(56) References Cited

U.S. PATENT DOCUMENTS

| 4,541,925 A | 9/1985 | Seiver et al. |
| 2003/0086839 A1* | 5/2003 | Rivin ................ B01J 19/10 422/186.01 |

(Continued)

FOREIGN PATENT DOCUMENTS

| DK | 2015 00118 A1 | 3/2015 |
| GB | 2 038 667 A | 7/1980 |

(Continued)

OTHER PUBLICATIONS

Danish Search Report of Danish Patent Application No. PA 2015 00662, dated Apr. 26, 2016.
(Continued)

*Primary Examiner* — Natasha E Young
(74) *Attorney, Agent, or Firm* — Buchanan Ingersoll & Rooney P.C.

(57) ABSTRACT

A reactor system for dehydrogenation of alkanes in a given temperature range upon bringing a reactant stream including alkanes into contact with a catalytic mixture. The reactor system includes a reactor unit arranged to accommodate the catalytic mixture, where the catalytic mixture includes catalyst particles and a ferromagnetic material. The catalyst particles are arranged to catalyze the dehydrogenation of alkanes. The ferromagnetic material is ferromagnetic at least
(Continued)

at temperatures up to an upper limit of the given temperature range. The reactor system moreover includes an induction coil arranged to be powered by a power source supplying alternating current and being positioned so as to generate an alternating magnetic field within the reactor unit upon energization by the power source, whereby the catalytic mixture is heated to a temperature within the temperature range by means of the alternating magnetic field. Also, a catalytic mixture and a method of dehydrogenating alkanes.

6 Claims, 3 Drawing Sheets

(51) Int. Cl.

| | | |
|---|---|---|
| B01J 19/00 | (2006.01) | |
| B01J 19/08 | (2006.01) | |
| B01J 23/08 | (2006.01) | |
| B01J 23/745 | (2006.01) | |
| B01J 23/825 | (2006.01) | |
| B01J 35/00 | (2006.01) | |
| B01J 35/02 | (2006.01) | |
| B01J 37/04 | (2006.01) | |
| B01J 37/34 | (2006.01) | |
| C07C 5/00 | (2006.01) | |
| C07C 5/333 | (2006.01) | |
| B01J 37/08 | (2006.01) | |

(52) U.S. Cl.
CPC ....... *B01J 35/0006* (2013.01); *B01J 35/0033* (2013.01); *B01J 35/026* (2013.01); *B01J 37/04* (2013.01); *B01J 37/342* (2013.01); *C07C 5/3335* (2013.01); *B01J 23/825* (2013.01); *B01J 37/08* (2013.01); *B01J 2208/00327* (2013.01); *B01J 2208/00433* (2013.01); *B01J 2219/00121* (2013.01); *B01J 2219/0854* (2013.01); *B01J 2219/0879* (2013.01); *C07C 2521/04* (2013.01); *C07C 2523/08* (2013.01); *C07C 2523/745* (2013.01); *C07C 2523/825* (2013.01); *Y02P 20/52* (2015.11)

(58) Field of Classification Search
CPC ... B01J 23/00; B01J 23/08; B01J 23/70; B01J 23/74; B01J 23/745; B01J 23/76; B01J 23/825; B01J 35/00; B01J 35/0006; B01J 35/002; B01J 35/0033; B01J 35/02; B01J 35/026; B01J 37/00; B01J 37/04; B01J 37/08; B01J 37/34–342; B01J 2208/00–00017; B01J 2208/00327; B01J 2208/00433; B01J 2219/00049; B01J 2219/00051; B01J 2219/00121; B01J 2219/08; B01J 2219/0801; B01J 2219/085; B01J 2219/0854; B01J 2219/0873; B01J 2219/0879; C07C 5/00; C07C 5/32; C07C 5/327; C07C 5/333; C07C 5/3335; C07C 2521/00–04; C07C 2523/00; C07C 2523/70–745; C07C 2523/76; C07C 2523/08; C07C 2523/825

See application file for complete search history.

(56) References Cited

U.S. PATENT DOCUMENTS

| | | |
|---|---|---|
| 2007/0179053 A1 | 8/2007 | Lee et al. |
| 2007/0204512 A1 | 9/2007 | Self et al. |
| 2010/0160705 A1* | 6/2010 | Kosters .................. B01J 8/062 585/654 |
| 2011/0265738 A1 | 11/2011 | Ichikawa et al. |
| 2011/0301363 A1 | 12/2011 | Friese et al. |
| 2012/0202994 A1 | 8/2012 | Friese et al. |
| 2012/0203021 A1 | 8/2012 | Friese et al. |
| 2012/0215023 A1 | 8/2012 | Friese et al. |
| 2015/0083572 A1 | 3/2015 | Handerek |
| 2018/0244592 A1* | 8/2018 | Hojlund Nielsen ..... B01J 37/04 |
| 2018/0311630 A1 | 11/2018 | Hojlund Nielsen et al. |

FOREIGN PATENT DOCUMENTS

| | | | | |
|---|---|---|---|---|
| GB | 2 210 286 A | | 6/1989 | |
| GB | 2210286 A | * | 6/1989 | ............ B01J 8/0285 |
| JP | 2013-111538 A | | 6/2013 | |

OTHER PUBLICATIONS

International Search Report (PCT/ISA/210) dated Jan. 20, 2017, by the European Patent Office as the International Searching Authority for International Application No. PCT/EP2016/075489.
Written Opinion (PCT/ISA/237) dated Jan. 20, 2017, by the European Patent Office as the International Searching Authority for International Application No. PCT/EP2016/075489.
Danish Search Report of Danish Patent Application No. PA 2015 00665, dated May 23, 2016.
International Search Report (PCT/ISA/210) dated Jan. 20, 2017, by the European Patent Office as the International Searching Authority for International Application No. PCT/EP2016/075491.
Written Opinion (PCT/ISA/237) dated Jan. 20, 2017, by the European Patent Office as the International Searching Authority for International Application No. PCT/EP2016/075491.

* cited by examiner

DEHYDROGENATION OF ALKANES

CROSS-REFERENCE TO RELATED APPLICATIONS

This application is the U.S. National Stage of International Application No. PCT/EP2016/075489, now WO 2017/072057, filed Oct. 24, 2016, and claims foreign priority of DKPA 2015 00662, filed on Oct. 28, 2015. The entire teachings of the above applications are incorporated herein by reference.

The present invention relates to a process for the dehydrogenation of alkanes, primarily the dehydrogenation of alkanes to alkenes and/or to dienes, such as dehydrogenation of ethane, propane and butane to the respective alkene products (olefins) ethylene, propylene and butylene, and dehydrogenation of e.g. n-butane to butadiene. More particularly, the process comprises heating a catalytic mixture within a reactor unit inductively. Moreover, the present invention comprises a reactor system for dehydrogenation of alkanes, and a catalytic mixture for catalyzing dehydrogenation of alkanes.

Current state of the art in industrial processes for dehydrogenation of alkanes are high temperature processes typically above 450° C. and in all cases also low pressure processes amounting from the fact that dehydrogenation reaction $AH_2=A+H_2$ is endothermic requiring about 125 kJ/mole and involves forming more product moles than reactants. Thus, both a temperature increase and low pressure lead to higher conversion. A is an unsaturated compound and as such highly reactive. The dehydrogenation of alkanes is normally carried out with hydrogen, nitrogen or steam as diluent, or without diluents.

One of the parasitic reactions in dehydrogenation is carbon formation, which leads to rapid deactivation of the catalyst. Thus, frequent regenerations of the catalyst may be necessary in certain applications. Carbon formation is not only a problem for the catalyst. Also the material used for the dehydrogenation reactor and for the piping has to be carefully selected, typically by using highly expensive alloys in order to avoid carbon attack resulting in the catastrophic form of corrosion known as metal dusting.

It is therefore an object of the present invention to provide a process, reactor system and catalytic mixture for dehydrogenation of alkanes to the corresponding unsaturated chemical products which is able to maintain a high stability of the catalyst.

It is another object of the present invention to provide a process, reactor system and catalytic mixture for dehydrogenation of alkanes to the corresponding unsaturated chemical products which is simple and energy efficient and which at the same time enables maintaining high stability of the catalyst.

It is also an object of the present invention to provide a process, reactor system and catalytic mixture wherein the reaction temperature is controlled accurately. Preferably, the temperature of the process is lowered compared to hitherto known reactions; hereby, the thermodynamic potential for dehydrogenation is increased and parasitic reactions, such as coking of the catalytic mixture and/or cracking of the reactant stream are reduced.

The present invention solves one or more of the above mentioned problems.

An aspect of the present invention relates to a reactor system for dehydrogenation of alkanes in a given temperature range T upon bringing a reactant stream comprising alkanes into contact with a catalytic mixture. The reactor system comprises a reactor unit arranged to accommodate the catalytic mixture, where the catalytic mixture comprises catalyst particles in intimate contact with ferromagnetic material, where the catalyst particles are arranged to catalyze the dehydrogenation of alkanes. The reactor system moreover comprises an induction coil arranged to be powered by a power source supplying alternating current and being positioned so as to generate an alternating magnetic field within the reactor unit upon energization by the power source, whereby the catalytic mixture is heated to a temperature within the temperature range T by means of the alternating magnetic field.

In the catalytic mixture, the catalyst particles and ferromagnetic material are in intimate contact. The effect of the catalyst particles and the ferromagnetic material of the system being in intimate contact is that the heat generated in the ferromagnetic material is conducted to the catalytic particles, either directly or indirectly via a reactant stream during operation, over a short distance. Therefore, the heating within the reactor system takes place at or very close to the catalyst particles. Thus, the temperature of the reactant stream may be lower, when the reactant stream reaches the catalytic mixture than when it leaves the catalytic mixture within the reactor system. This gives less problems with cracking and coking within the reactor system. The term "catalyst particles in intimate contact with a ferromagnetic material" is meant to denote that catalyst particles are in substantial proximity to the ferromagnetic material, such as in a physical mixture together with the ferromagnetic material, in physical contact with the ferromagnetic material or supported on the ferromagnetic material, possibly via an oxide.

A key element which the present invention addresses is the issue of supplying heat needed to carry out the dehydrogenation reaction. The reaction has traditionally been carried out in more than one adiabatic catalytic bed, with reheating in between or in a reactor with a furnace, e.g. an electric furnace. By the reactor system of the invention, the heat for the endothermic dehydrogenation reaction is provided by induction heating. This provides for a quick heating of the catalyst within the reactor. Moreover, a good control of the temperature within the reactor system is obtained, which in turn assists in reducing carbon formation on the catalyst and in maximizing the conversion of alkanes to alkenes and/or dienes.

In general, the temperature within the reactor unit may be kept lower than with an externally heated reactor. This provides for an improved overall yield, a better selectivity as well as a quicker start-up of the process. Moreover, less catalyst degeneration in the form of coking and cracking will happen, thus reducing the frequency of regenerations of the catalyst.

The Curie temperature of the ferromagnetic material may be close to, above or far above the upper limit of the given temperature range T. However, the Curie temperature could be slightly lower than the upper limit of the given temperature range T, in that the reactant gas stream entering the reactor system may be heated to a temperature above the Curie temperature before entering the reactor system, thereby providing an upper limit of the temperature range T—in an upstream part of the reactor unit—which is higher than that obtainable by induction heating. As used herein, the term "temperature range T" is meant to denote a desired range of temperatures, typically up to an upper limit thereof, at which the dehydrogenation reaction is to take place within the reactor system during operation.

Preferably, the coercivity of the ferromagnetic material is high, so that the amount of heat generated within the ferromagnetic material and dissipated by the external field in reversing the magnetization in each magnetization cycle is high.

As used herein, a material of "high magnetic coercivity", $_BH_C$, is seen as a "hard magnetic material" having a coercivity $_BH_C$ at or above about 20 kA/m, whilst a material of "low magnetic coercivity" is seen as a "soft magnetic material" having a coercivity $_BH_C$ at or below about 5 kA/m. It should be understood that the terms "hard" and "soft" magnetic materials are meant to refer to the magnetic properties of the materials, not their mechanical properties.

Ferromagnetic material provides for further advantages, such as:
- A ferromagnetic material absorbs a high proportion of the magnetic field, thereby making the need for shielding less or even superfluous.
- Heating of ferromagnetic materials is relatively faster and cheaper than heating of non-ferromagnetic materials. A ferromagnetic material has an inherent or intrinsic maximum temperature of heating, viz. the Curie temperature.

Therefore, the use of a catalytic mixture which is ferromagnetic ensures that an endothermic chemical reaction is not heated above a specific temperature, viz. the Curie temperature. Thus, it is ensured that the chemical reaction will not run out of control.

Another advantage of the invention is that the temperature of the reactor unit can be kept lower than the temperature of the conventionally used adiabatic reactor. The lower temperature is beneficial for the overall yield of the process and required regenerations for carbon removal will be less frequent since parasitic reactions like coking and cracking are reduced. Further advantages comprise the possibility of tuning the exit temperature, which increase the thermodynamic potential for dehydrogenation.

In conclusion, the invention provides a reactor system arranged to carry out dehydrogenation of alkanes to alkenes and/or dienes cheaper and with better selectivity than current reactor systems. Moreover, the lifetime of the catalyst will be improved due to the lower average operation temperature within the reactor system.

The induction coil may e.g. be placed within the reactor unit or around the reactor unit. If the induction coil is placed within the reactor unit, it is preferable that it is positioned at least substantially adjacent to the inner wall(s) of the reactor unit in order to surround as much of the catalytic mixture as possible. In the cases, where the induction coil is placed within the reactor unit, windings of the reactor unit may be in physical contact with catalytic mixture. In this case, in addition to the induction heating, the catalytic mixture may be heated directly by ohmic/resistive heating due to the passage of electric current through the windings of the induction coil. The reactor unit is typically made of non-ferromagnetic material.

In an embodiment, the given temperature range T is the range between about 350° C. and about 700° C. or a sub-range thereof. In an embodiment, the Curie temperature of the ferromagnetic material is in the range from about 600° C. to about 700° C.

In an embodiment, the Curie temperature of the ferromagnetic material equals an operating temperature at substantially the upper limit of the given temperature range T of the dehydrogenation reaction. Hereby, it is ensured that the dehydrogenation reaction is not heated above a specific temperature, viz. the Curie temperature. Thus, it is ensured that the temperature becomes too high; it is well known that excessive temperatures may give rise to significant coke formation due to thermal cracking. Thus, designing the composition of the catalyst in order to design the Curie temperature renders it possible to provide a catalyst that will be less prone to carbon formation.

In an embodiment, the induction coil is placed within the reactor unit or around the reactor unit. The coil may e.g. be made of an iron-chromium-aluminum (FeCrAl) alloy, such as kanthal.

In an embodiment, the catalyst particles are supported on the ferromagnetic material. The ferromagnetic material may e.g. comprise one or more ferromagnetic macroscopic supports susceptible for induction heating, where the one or more ferromagnetic macroscopic supports are ferromagnetic at temperatures up to an upper limit of the given temperature range T, where the one or more ferromagnetic macroscopic supports is/are coated with an oxide and where the oxide is impregnated with the catalyst particles.

The oxide may also be impregnated with ferromagnetic particles. Thus, when the catalyst particles are subjected to a varying magnetic field, both the ferromagnetic macroscopic support and the ferromagnetic particles impregnated into the oxide of the ferromagnetic macroscopic support are heated. Whilst the ferromagnetic macroscopic support heats the catalyst particles from within, the ferromagnetic particles heats from the outside of the oxide. Thereby, a higher temperature and/or a higher heating rate are/is achievable.

As used herein, the term "macroscopic support" is meant to denote a macroscopic support material in any appropriate form providing a high surface. Non-limiting examples are metallic elements, monoliths or miniliths. The macroscopic support may have a number of channels; in this case it may be straight-channeled or a cross-corrugated element. The material of the macroscopic support may be porous or the macroscopic support may be a solid. The word "macroscopic" in "macroscopic support" is meant to specify that the support is large enough to be visible with the naked eye, without magnifying devices.

In an embodiment, catalyst particles and ferromagnetic particles are mixed and treated to provide bodies of catalytic mixture. The magnitude of the size of the catalyst and ferromagnetic particles is in the micrometer scale, such that a characteristic size of the particles is larger than 0.1 µm. The size of particles of ferromagnetic material needs to be sufficient for ferromagnetic heating to take place. This is e.g. described in "Magnetic multi-granule nanoclusters: A model system that exhibits universal size effect of magnetic coercivity", by Ji Sung Lee et al, Scientific Report, published 17 Jul. 2015 (see e.g. FIG. 1). Preferably, the smallest outside dimension of the bodies is between about 2-3 mm and about 8 mm. The ratio between catalyst particles and ferromagnetic particles may e.g. be 1:1. Alternatively, the powder mixture may comprise more ferromagnetic particles than catalyst particles, depending on the bodies.

In an embodiment, the catalytic mixture comprises bodies of catalyst particles mixed with bodies of ferromagnetic material, wherein the smallest outside dimension of the bodies is in the order of about 1-2 mm or larger. Preferably, the smallest outside dimension of the bodies is between about 2-3 mm and about 8 mm. The bodies of catalyst particles are e.g. extrudates or miniliths. The bodies of ferromagnetic material may e.g. be iron spheres. The term "miniliths" is meant to denote a small monolith; a reactor may typically house a large number of miniliths.

The catalytic mixture preferably has a predetermined ratio between the catalyst particles and the ferromagnetic material. In an embodiment, the predetermined ratio is a predetermined graded ratio varying along a flow direction of the reactor. Hereby, it is possible to control the temperature in different zones of the reactor. A radial flow reactor may be used; in this case, the predetermined ration varies along the radial direction of the reactor. Alternatively, an axial flow reactor may be used.

Another aspect of the invention relates to a catalytic mixture arranged for catalyzing dehydrogenation of alkanes in a reactor in a given temperature range T upon bringing a reactant stream comprising alkanes into contact with the catalytic mixture. The catalytic mixture comprises catalyst particles in intimate contact with a ferromagnetic material, where the catalyst particles are arranged to catalyze the dehydrogenation of alkanes. The catalytic mixture may have a predetermined ratio between the catalyst and the ferromagnetic material.

In an embodiment, the Curie temperature of the ferromagnetic material substantially equals an operating temperature at substantially the upper limit of the given temperature range T of the dehydrogenation reaction. Alternatively, the Curie temperature could be slightly lower than the upper limit of the given temperature range T, in that the reactant gas stream entering the reactor system may be heated to a temperature above the Curie temperature before entering the reactor system, thereby providing an upper limit of the temperature range T—in an upstream part of the reactor unit—which is higher than that obtainable by induction heating.

In an embodiment, the ferromagnetic material is a material comprising iron, an alloy comprising iron and chromium, an alloy comprising iron, chromium and aluminum, an alloy comprising iron and cobalt, or an alloy comprising iron, aluminum, nickel and cobalt. In an embodiment, the catalyst particles comprise gallium, a noble metal catalyst, a metallic sulfide or $Cr_2O_3$. The catalyst particles may be promoted with appropriate promoters, e.g. gallium may be promoted with platinum. The catalyst particles may be impregnated on to a carrier. The metal of the metallic sulfide may e.g. be Fe, Co, Ni, Mn, Cu, Mo, W and combinations thereof.

In an embodiment, the catalyst particles are supported on the ferromagnetic material. For example, the ferromagnetic material comprises one or more ferromagnetic macroscopic supports susceptible for induction heating, where the one or more ferromagnetic macroscopic supports is/are coated with an oxide and where the oxide is impregnated with catalyst particles. Non-limiting examples of ferromagnetic macroscopic supports coated with an oxide, which in turn is impregnated with catalyst particles, are metallic elements, monoliths or miniliths.

The Curie temperature of the ferromagnetic material may substantially equal an operating temperature at or above the upper limit of the given temperature range T of the dehydrogenation reaction. Alternatively, the Curie temperature could be slightly lower than the upper limit of the given temperature range T, in that the reactant gas stream entering the reactor system may be heated to a temperature above the Curie temperature before entering the reactor system, thereby providing an upper limit of the temperature range T—in an upstream part of the reactor unit—which is higher than that obtainable by induction heating.

In an embodiment, the catalytic mixture has a predetermined ratio between the catalyst and the ferromagnetic materials. The predetermined ratio between the catalyst and the ferromagnetic materials may be a predetermined graded ratio varying along a flow direction of the reactor. Hereby, when the catalytic mixture is used in a reactor, it is possible to control the temperature in different zones of the reactor. A radial flow reactor may be used; in this case, the predetermined ratio varies along the radial direction of the reactor.

In an embodiment, catalyst particles and ferromagnetic particles are mixed and treated to provide bodies of catalytic mixture, the bodies having a predetermined ratio between catalyst and ferromagnetic particles. In an embodiment, the catalytic mixture comprises bodies of catalyst particles mixed with bodies of ferromagnetic particles. Such bodies may e.g. be pellets, extrudates or miniliths.

Another aspect of the invention relates to a method for dehydrogenating of alkanes in a given temperature range T in a reactor system. The reactor system comprises a reactor unit arranged to accommodate a catalytic mixture. The catalytic mixture comprises catalyst particles in intimate contact with a ferromagnetic material, where the catalyst particles are arranged to catalyze the dehydrogenation of alkanes. The catalytic mixture has a predetermined ratio between the catalyst and the ferromagnetic materials. An induction coil is arranged to be powered by a power source supplying alternating current and positioned so as to generate an alternating magnetic field within the reactor unit upon energization by the power source, whereby the catalytic mixture is heated to a temperature within the given temperature range T by means of the alternating magnetic field. The method comprises the steps of:
 (i) Generating an alternating magnetic field within the reactor unit upon energization by a power source supplying alternating current, the alternating magnetic field passing through the reactor unit, thereby heating catalytic mixture by induction of a magnetic flux in the material;
 (ii) bringing a reactant stream comprising alkanes into contact with the catalyst particles;
 (iii) heating the reactant stream within the reactor by the generated alternating magnetic field; and
 (iv) letting the reactant stream react in order to provide a product stream to be outlet from the reactor.

The sequence of the steps (i) to (iv) is not meant to be limiting. Steps (ii) and (iii) may happen simultaneously, or step (iii) may be initiated before step (ii) and/or take place at the same time as step (iv). Advantages as explained in relation to the reactor system and the catalytic mixture also apply to the method for dehydrogenating alkanes. The catalytic mixture may have a predetermined ratio between the catalyst particles and the ferromagnetic material.

The Curie temperature of the ferromagnetic material may be equal to or above an upper limit of the given temperature range T of the dehydrogenation reaction. Alternatively, the Curie temperature could be slightly lower than the upper limit of the given temperature range T, in that the reactant gas stream entering the reactor system may be heated to a temperature above the Curie temperature before entering the reactor system, thereby providing an upper limit of the temperature range T—in an upstream part of the reactor unit—which is higher than that obtainable by induction heating.

DETAILED DESCRIPTION OF THE FIGURES

Figure 1:
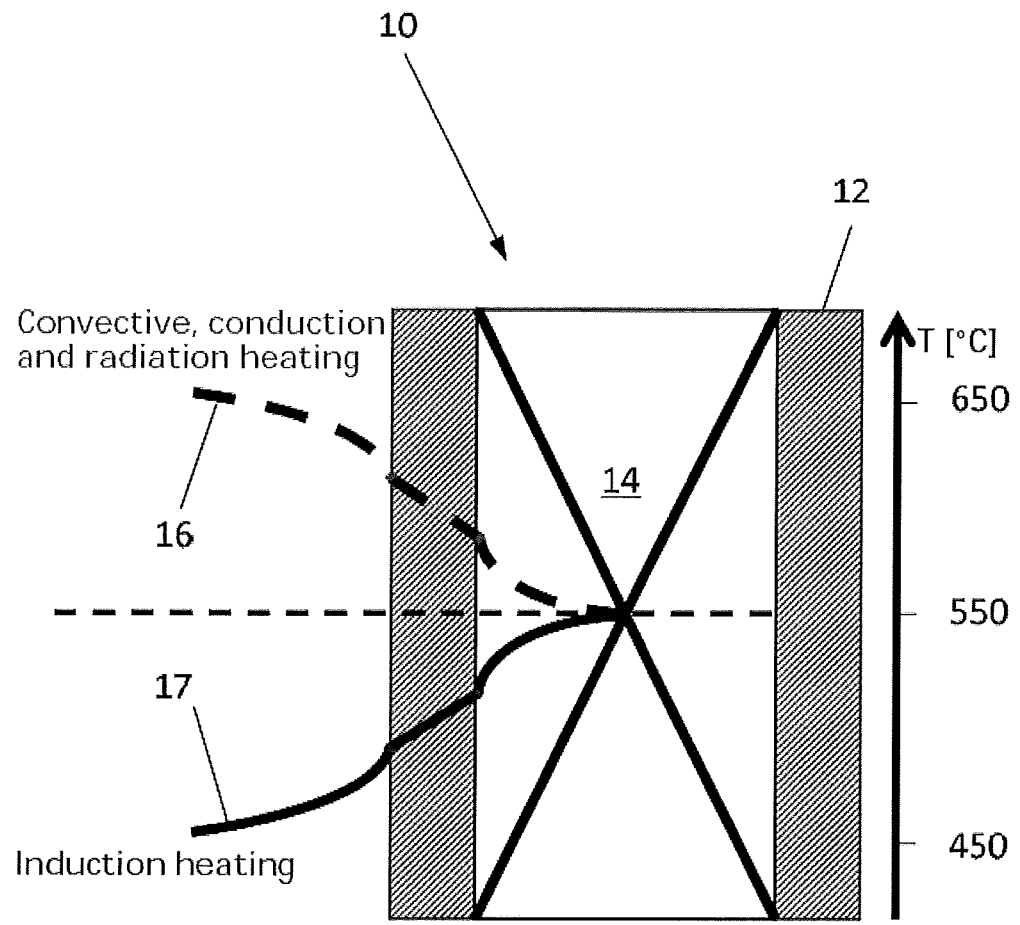
FIG. 1 show temperature profiles of a reactor unit heated by convective/conductive and/or radiation heating, and induction heating, respectively.

FIG. 1 is a graph showing temperature profiles of a reactor unit 10 heated by convective/conductive and/or radiation heating, and induction heating, respectively, during an endothermic reaction within the reactor unit 10. The temperature profiles in FIG. 1 are indicated together with a schematic cross-section through a reactor unit 10 having walls 12 holding a catalyst bed 14 with a catalytic mixture for endothermic reactions. In the case of induction heating, the catalyst mixture in the catalyst bed 14 is susceptible to inductive heating. Means for heating the reactor unit 10 and/or the catalyst bed 14 are not shown. In the case of convective, conduction and/or radiation heating, the means for heating could e.g. be fired burners; means for induction heating would typically be an electromagnet, e.g. an induction coil. A temperature scale is indicated at the right side of FIG. 1. The reactor unit 10 is an axial flow reactor unit and the temperature profiles shown in FIG. 1 indicate the temperatures at the center of the catalyst bed within the reactor unit. The horizontal dotted line indicates a temperature of 550° C. at the centre of the catalyst bed both in the case of convective, conduction and radiation heating (curve 16) and induction heating (curve 17). The dotted curve 16 indicates the temperatures outside the reactor unit, at the reactor unit walls as wells as within the catalyst bed 14 when heated by convective/conductive and/or radiation heating, whilst the solid curve 17 indicate the temperatures outside the reactor unit, at the reactor unit walls as well as within the catalyst bed 14 when heated by convective/conductive and/or radiation heating, and induction heating, respectively.

It is clear from FIG. 1, that in the case of convective/conductive and/or radiation heating, the temperature is higher outside the wall 12 than within the wall 12, and that the temperature within the catalyst bed 14 is lower than that at the wall 12. At the center of the catalyst bed, the temperature is at its lowest. This is because the temperature at the heat source must be higher than the reaction zone and due to the temperature loss through the walls and due to the endothermic nature of the reaction within the reactor unit 10. In contrast, the temperature profile as indicated by the curve 17 shows that for induction heating the temperature is higher at the wall 12 compared to outside the reactor unit, whilst the temperature inside the catalyst bed increases from the wall 12 to the center of the catalyst bed 14.

In general, performing endothermic reactions is limited by how efficient heat can be transferred to the reactive zone of the catalyst bed 14. Conventional heat transfer by convection/conduction/radiation can be slow and will often meet large resistance in many configurations. Moreover, heat losses within the walls of the reactor play a role. In contrast, when heat is deposited inside the catalyst bed 14 by the induction concept, the catalyst bed will be the hottest part of the reactor 10 in contrast to conventional heating where the exterior heat source has to be significantly hotter than the internal part to have a driving mechanism for the heat transfer.

To make the catalyst bed susceptible for induction, different approaches may be applied. One approach is to heat the catalyst by induction by making the catalytically active particles of the catalyst ferromagnetic at reaction temperatures.

In addition to the possibility of delivering heat directly to the catalyst mixture, induction heating offers a fast heating mechanism, which potentially could make upstart of a dehydrogenation reactor relative fast.

Figure 2:
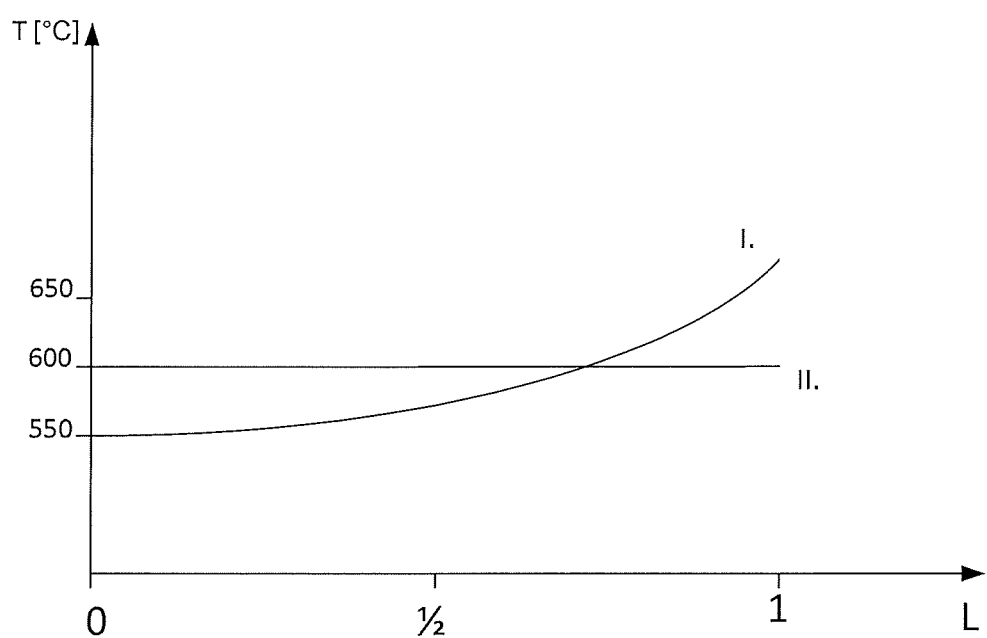
FIG. 2 shows temperature profiles along the length of an inductively heated axial reactor unit according to the invention.

FIG. 2 shows temperature profiles along the length of an inductively heated axial reactor unit according to the invention. FIG. 2 shows two different temperature profiles: an isothermal profile I. and an increasing temperature profile II, along the axial direction of the reactor unit. The reactant stream reaches the catalytic mixture at the reactor length L=0 and leaves the catalytic mixture at the reactor length L=1. In the isothermal profile I, the temperature is held constant throughout the reactor length. This is achievable by designing the induction coil and/or the catalytic mixture accordingly. In the temperature profile II, the temperature increases along the path of the reactant stream through the reactor unit. This is advantageous, in that a relatively low inlet temperature (at L=0), reduces the risk of cracking of the reactant stream, and in that a high temperature towards the end of the reactor unit (L=1) provides an improved thermodynamic equilibrium for the dehydrogenation reaction. In the temperature profile II, it is noted that the maximum reactant stream temperature is the outlet temperature. Even though FIG. 2 is shown for an axial flow reactor unit, similar profiles are relevant for radial flow reactor units along the path of the reactant stream through the catalytic mixture.

Figure 3A:
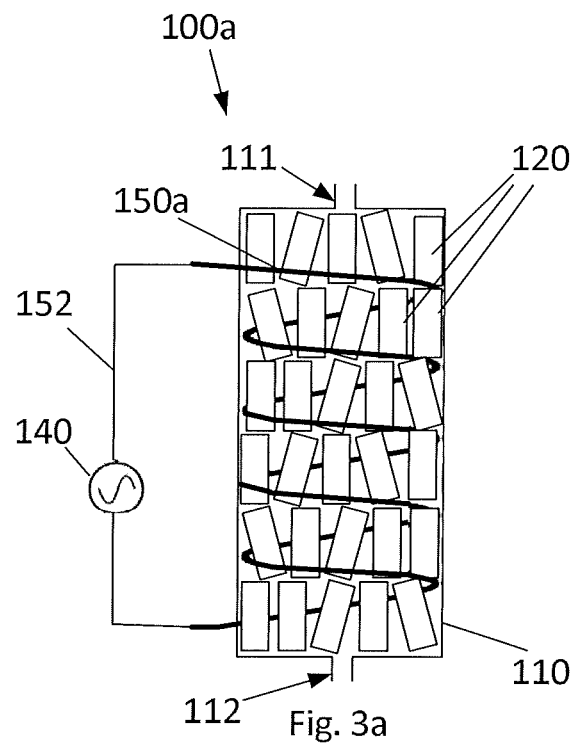
FIGS. 3a and 3b show schematic drawings of two embodiments of a reactor system.
Figure 3B:
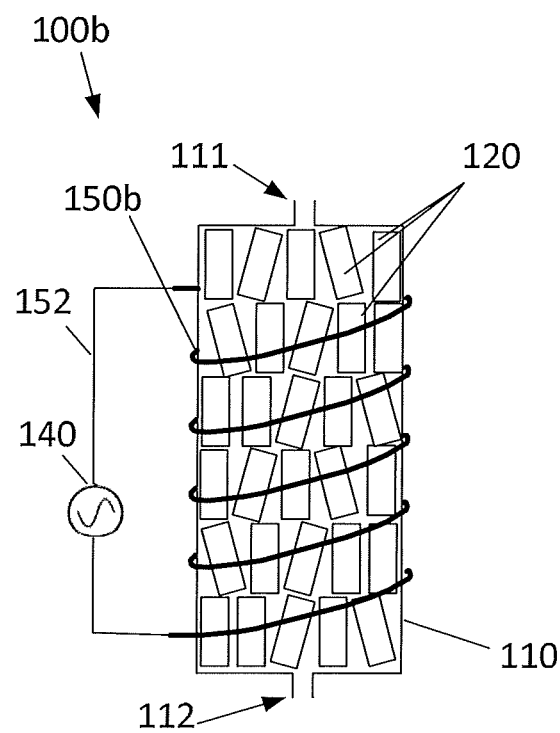

FIGS. 3a and 3b show schematic drawings of five embodiments 100a and 100b, of a reactor system. In FIGS. 3a and 3b, similar features are denoted using similar reference numbers.

FIG. 3a shows an embodiment of the reactor system 100a for carrying out dehydrogenation of alkanes upon bringing a reactant stream comprising alkanes into contact with a catalytic mixture 120. The reactor system 100a comprises a reactor unit 110 arranged to accommodate a catalytic mixture 120 comprising catalyst particles and a ferromagnetic material, where the catalyst particles are arranged to catalyze the dehydrogenation of alkanes to alkenes and/or dienes and the ferromagnetic material is ferromagnetic at least at temperatures up to about 500° C. or 700° C.

Reactant is introduced into the reactor unit 110 via an inlet 111, and reaction products formed on the surface of the catalytic mixture 120 are outlet via an outlet 112.

The reactor system 100a further comprises an induction coil 150a arranged to be powered by a power source 140 supplying alternating current. The induction coil 150a is connected to the power source 140 by conductors 152. The induction coil 150a is positioned so as to generate an alternating magnetic field within the reactor unit 110 upon energization by the power source 140. Hereby the catalytic mixture 120 is heated to a temperature within a given temperature range T relevant for dehydrogenation of alkanes, such as between 350° C. and about 500° or 700° C., by means of the alternating magnetic field.

The induction coil 150a of FIG. 3a is placed substantially adjacent to the inner surface of the reactor unit 110 and in physical contact with the catalytic mixture 120. In this case, in addition to the induction heating provided by the magnetic field, the catalyst particles 120 adjacent the induction coil 150a are additionally heated directly by ohmic/resistive heating due to the passage of electric current through the windings of the induction coil 150a. The induction coil 150a may be placed either inside or outside the catalyst basket (not shown) supporting the catalytic mixture 120 within the reactor unit 110. The induction coil is preferably made of kanthal.

The catalytic mixture 120 may be divided into sections (not shown in the figures), where the ratio between the catalytic material and the ferromagnetic material varies from one section to another. At the inlet of the reactor unit 110, the reaction rate is high and the heat demand is large; this may be compensated for by having a relatively large proportion of ferromagnetic material compared to the catalytic material. The ferromagnetic material may also be designed to limit the temperature by choosing a ferromagnetic material with a Curie temperature close to the desired reaction temperature.

Placing the induction coil 150a within the reactor unit 110 ensures that the heat produced due to ohmic resistance heating of the induction coil 150a remains useful for the dehydrogenation reaction. However, having an oscillating magnetic field within the reactor may cause problems, if the materials of the reactor unit 110 are magnetic with a high coercivity, in that undesirably high temperatures may be the result. This problem can be circumvented by cladding the inside of the reactor unit 110 with materials capable of reflecting the oscillating magnetic field. Such materials could e.g. be good electrical conductors, such as copper. Alternatively, the material of the reactor unit 110 could be chosen as a material with a very low coercivity. Alternatively, the induction coil 150 could be wound as a torus.

To make the catalyst bed susceptible for induction, different approaches may be applied. One approach is to support the catalyst particles on the ferromagnetic material. For example, the ferromagnetic material comprises one or more ferromagnetic macroscopic supports susceptible for induction heating, and the one or more ferromagnetic macroscopic supports are ferromagnetic at temperatures up to an upper limit of the given temperature range T. The one or more ferromagnetic macroscopic supports is/are coated with an oxide and the oxide is impregnated with catalyst particles. Another approach is to mix catalyst particles and ferromagnetic particles and treat the mixture to provide bodies of catalytic mixture. Additionally or alternatively, the catalytic mixture comprises bodies of catalyst particles mixed with bodies of ferromagnetic material, wherein the smallest outside dimension of the bodies are in the order of about 1-2 mm or larger.

The catalyst particles may comprise gallium, a noble metal catalyst, a metallic sulfide or $Cr_2O_3$. The catalyst particles may be impregnated on to a carrier. The catalyst particles may be promoted with an appropriate promoter, for example gallium could be promoted with platinum. The metal of the metallic sulfide may e.g. be Fe, Co, Ni, Mn, Cu, Mo, W and combinations thereof. The catalyst particles may be mixed with a ferromagnetic material with a high coercivity and a high Curie temperature, such as AlNiCo or Permendur.

The catalytic mixture preferably has a predetermined ratio between the catalyst particles and the ferromagnetic material. This predetermined ratio may be a graded ratio varying along a flow direction of the reactor.

In another approach, ferromagnetic macroscopic supports are coated with an oxide impregnated with the catalytically active material. This approach offers a large versatility compared to the ferromagnetic nanoparticles in the catalyst, as the choice of catalytic active phase is not required to be ferromagnetic.

FIG. 3b shows another embodiment 100b of the reactor system for carrying out dehydrogenation of alkanes upon bringing a reactant stream comprising alkanes into contact with a catalytic mixture 120. The reactor unit 110 and its inlet and outlet 111, 112, the catalytic mixture 120, the power source 140 and its connecting conductors 152 are similar to those of the embodiment shown in FIG. 3a.

In the embodiment of FIG. 3b, an induction coil 150b is wound or positioned around the outside of the reactor unit 110.

In both embodiments shown in FIGS. 3a-3b, the catalytic mixture can be any catalytic mixture according to the invention. Thus, the catalytic mixture may be in the form of catalyst particles supported on the ferromagnetic material, e.g. where in the form of ferromagnetic macroscopic support(s) coated with an oxide, where the oxide is impregnated with catalyst particles, miniliths, a monolith, or bodies produced from a mixture of catalyst particles powder and ferromagnetic material powder. Thus, the catalytic mixture is not limited to catalytic mixture having relative size as compared to the reactor system as shown in the figures. Moreover, when the catalytic mixture comprises a plurality of macroscopic supports, the catalytic mixture would typically be packed so as to leave less space between the macroscopic supports than shown in the FIGS. 3a and 3b. Furthermore, in the two embodiments shown in FIGS. 3a and 3b, the reactor unit 110 is made of non-ferromagnetic material. In the two embodiments shown in FIGS. 3a and 3b, the power source 140 is an electronic oscillator arranged to pass a high-frequency alternating current (AC) through the coil surrounding at least part of the catalyst particles within the reactor system.

EXAMPLE

Catalyst bodies for propane dehydrogenation reaction are made by impregnating an alumina carrier with gallium, typically about 1 wt % gallium. The alumina carrier may be shaped as a cylinder or as an extrudate with an equivalent diameter around 3 mm. The catalyst bodies are physically mixed with ferromagnetic material having a high coercivity and a Curie temperature above about 600° C. The ferromagnetic material may e.g. be a cast iron or Alnico pretreated by oxidation in steam and hydrogen at temperatures above 700° C. Preferably, the ferromagnetic material could be ferromagnetic bodies in the form of small galvanized iron spheres, using either tin or zinc as galvanizing agent. The iron oxide may e.g. be magnetite and should have a suitable coercivity, e.g. a relatively high magnetic coercivity, $_BH_C$, e.g. $_BH_C$>20 kA/m.

The catalyst bodies and the ferromagnetic material, e.g. galvanized iron spheres, are physically mixed. The mixing can be graded so the concentration of ferromagnetic material in the mixture differs throughout the path of the reactant stream through the reactor unit, viz. along the length of the reactor unit in the case of an axial flow reactor unit. For example, in the inlet region of the reactor unit, where the heat consumption is the highest due to heating of the incoming gas stream as well as conversion of the incoming gas stream, the catalytic mixture may be arranged to have a relatively higher amount of heat generating material, viz. ferromagnetic material, compared to sections of the reactor unit further downstream. Alternatively, in the inlet region of the reactor unit, the concentration of ferromagnetic material in the catalytic mixture may be lower than downstream sections of the reactor unit, since it may be advantageous to have a temperature gradient within the reactor unit where the temperature increases along the path of the reactant stream through the reactor unit. This is due to the fact that a low temperature at the inlet region of the reactor unit reduces the risk of cracking of the reactant stream. Moreover, a higher temperature towards the outlet region of the reactor units provides a better thermodynamic equilibrium. Thus, the grading of the ferromagnetic material within the catalytic mixture may be used to optimize the exit temperature, giving a high thermodynamic potential for conversion. Ideally the choice of material with high coercivity may be used to tune the exit temperature, since no heat will be generated above the Curie temperature. This will furthermore remove the risk of overheating the catalyst bodies, with resulting reduced parasitic reaction such as coking and cracking.

For propane dehydrogenation, the catalytic bodies within the reactor are preheated to 580° C. and kept at this temperature by means of inductive heating. The propane gas for dehydrogenation, which could be diluted with a carrier gas, typically nitrogen, hydrogen or steam, is preheated by a feed effluent heat exchanger to about 500° C. The pressure is kept around 1 bar by pumping on the exit stream. The reaction mixture is further heated as the dehydrogenation takes place. If equilibrated at 550° C. a pure $C_3H_8$ gas will experience a 36% conversion into propene and hydrogen. The resulting reaction product outlet from the reactor unit is cooled by heat exchange.

Even though the present invention has been described in connection with dehydrogenation of alkanes, primarily the dehydrogenation of alkanes to alkenes and/or to dienes, it should be noted that the invention is also suitable for dehydrogenation of other hydrocarbons.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. Furthermore, individual features mentioned in different claims may possibly be advantageously combined, and the mentioning of these features in different claims does not exclude that a combination of features is not possible and advantageous.

The invention claimed is:

1. A method for dehydrogenating of alkanes in a given temperature range T in a reactor system, said reactor system comprising a reactor unit arranged to accommodate a catalytic mixture, said catalytic mixture comprising catalyst particles in intimate contact with a ferromagnetic material, wherein said catalyst particles are arranged to catalyze the dehydrogenation of alkanes, and said ferromagnetic material is ferromagnetic at least at temperatures up to an upper limit of the given temperature range T, and an induction coil arranged to be powered by a power source supplying alternating current and positioned so as to generate an alternating magnetic field within the reactor unit upon energization by the power source, whereby the catalytic mixture is heated to a temperature within the given temperature range T by means of said alternating magnetic field, said method comprising the steps of:

(i) generating an alternating magnetic field within the reactor unit upon energization by a power source supplying alternating current, said alternating magnetic field passing through the reactor unit, thereby heating catalytic mixture by induction of a magnetic flux in the material;

(ii) bringing a reactant stream comprising alkanes into contact with said catalyst particles;

(iii) heating said reactant stream within said reactor by the generated alternating magnetic field; and (iv) letting the reactant stream react in order to provide a product stream to be outlet from the reactor, wherein the catalytic mixture is selected from one of the following:

wherein the catalytic mixture comprises catalyst particles and ferromagnetic particles that are mixed and treated to provide bodies of catalytic mixture, said bodies having a predetermined ratio between catalyst and ferromagnetic particles, wherein said catalytic mixture comprises bodies of catalyst particles mixed with bodies of ferromagnetic material, wherein the smallest outside dimension of the bodies is in the order of about 1-2 mm or larger, or wherein said ferromagnetic material comprises one or more ferromagnetic macroscopic supports susceptible for induction heating, wherein said one or more ferromagnetic macroscopic supports are ferromagnetic at temperatures up to an upper limit of the given temperature range T, wherein said one or more ferromagnetic macroscopic supports is/are coated with an oxide and wherein the oxide is impregnated with catalyst particles.

2. The method according to claim 1, wherein the temperature range T is the range from between about 350° C. and about 700° C.

3. The method according to claim 1, wherein the reactant stream is preheated in a heat exchanger prior to step (ii).

4. The method according to claim 1, wherein the catalytic mixture is wherein catalyst particles and ferromagnetic particles are mixed and treated to provide bodies of catalytic mixture, said bodies having a predetermined ratio between catalyst and ferromagnetic particles.

5. The method according to claim 1, wherein the catalytic mixture is wherein said catalytic mixture comprises bodies of catalyst particles mixed with bodies of ferromagnetic material, wherein the smallest outside dimension of the bodies is in the order of about 1-2 mm or larger.

6. The method according to claim 1, wherein the catalytic mixture is wherein said ferromagnetic material comprises one or more ferromagnetic macroscopic supports susceptible for induction heating, wherein said one or more ferromagnetic macroscopic supports are ferromagnetic at temperatures up to an upper limit of the given temperature range T, wherein said one or more ferromagnetic macroscopic supports is/are coated with an oxide and wherein the oxide is impregnated with catalyst particles.

* * * * *